US009566089B2

(12) United States Patent
Webb et al.

(10) Patent No.: US 9,566,089 B2
(45) Date of Patent: *Feb. 14, 2017

(54) EXTERNAL FIXATION ASSEMBLY AND METHOD OF USE

(71) Applicant: Wake Forest University Health Sciences, Winston-Salem, NC (US)

(72) Inventors: Lawrence X. Webb, Macon, GA (US); Louis C. Argenta, Winston-Salem, NC (US); Michael J. Morykwas, Winston-Salem, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 85 days.

This patent is subject to a terminal disclaimer.

(21) Appl. No.: 14/714,678

(22) Filed: May 18, 2015

(65) Prior Publication Data

US 2015/0245854 A1    Sep. 3, 2015

Related U.S. Application Data

(60) Continuation of application No. 13/896,750, filed on May 17, 2013, now Pat. No. 9,050,136, which is a
(Continued)

(51) Int. Cl.
*A61B 17/70*    (2006.01)
*A61B 17/66*    (2006.01)
(Continued)

(52) U.S. Cl.
CPC .............. *A61B 17/66* (2013.01); *A61B 17/60* (2013.01); *A61B 17/864* (2013.01); *A61B 17/866* (2013.01);
(Continued)

(58) Field of Classification Search
CPC ..... A61B 17/60; A61B 17/64; A61B 17/6425; A61B 17/6433; A61B 17/6441; A61B 17/645; A61B 17/6458; A61B 17/6466; A61B 17/6475; A61B 17/6483; A61B 17/6491; A61B 17/66; A61B 17/7098; A61B 17/864
See application file for complete search history.

(56) References Cited

U.S. PATENT DOCUMENTS 4,653,489 A * 3/1987 Tronzo ................. A61B 17/746
606/304
5,047,030 A * 9/1991 Draenert .............. A61B 10/025
606/304
(Continued)

*Primary Examiner* — Lynnsy Summitt
(74) *Attorney, Agent, or Firm* — Niels Haun; Dann, Dorfman, Herrell and Skillman, P.C.

(57) ABSTRACT

An external fixation assembly includes a plurality of hollow pins that are inserted into a patient's bone. Each pin has an interior bore and a plurality of apertures extending through the pin wall from the bore. The pin may be coupled to a source of vacuum pressure operable to create reduced pressure in the tissue surrounding the pin. A cover is placed around the pin and sealed to provide a fluid-tight enclosure that maintains reduced pressure around the pin. A method for applying external fixation using the fixator pins described above includes the steps of inserting each pin through a skin opening, positioning the pin apertures near selected tissue, covering the skin opening with a sealed enclosure, connecting the pins to a source of vacuum pressure, and activating the source of vacuum pressure to create reduced pressure in the patient's tissue at or near the bone.

2 Claims, 9 Drawing Sheets

Related U.S. Application Data continuation of application No. 13/094,233, filed on Apr. 26, 2011, now Pat. No. 8,454,603, which is a division of application No. 11/694,395, filed on Mar. 30, 2007, now Pat. No. 7,931,651.

(60) Provisional application No. 60/866,327, filed on Nov. 17, 2006.

(51) Int. Cl.
   *A61B 17/60* (2006.01)
   *A61B 17/86* (2006.01)
   *A61B 17/00* (2006.01)

(52) U.S. Cl.
   CPC .. *A61B 17/8685* (2013.01); *A61B 2017/00544* (2013.01)

(56) References Cited

U.S. PATENT DOCUMENTS

| | | | | |
|---|---|---|---|---|
| 5,098,435 A * | 3/1992 | Stednitz | A61B 17/1637 | 411/387.5 |
| 5,129,904 A * | 7/1992 | Illi | A61B 17/683 | 606/151 |
| 5,334,204 A * | 8/1994 | Clewett | A61B 17/8625 | 606/312 |
| 5,456,267 A * | 10/1995 | Stark | A61B 17/3472 | 128/898 |
| 5,743,912 A * | 4/1998 | Lahille | A61B 17/746 | 606/290 |
| 5,871,484 A * | 2/1999 | Spievack | A61B 17/72 | 604/285 |
| 6,048,343 A * | 4/2000 | Mathis | A61B 17/7098 | 606/304 |
| 6,086,589 A * | 7/2000 | Kuslich | A61B 17/70 | 606/247 |
| 6,210,376 B1 * | 4/2001 | Grayson | A61B 17/3472 | 604/264 |
| 6,214,012 B1 * | 4/2001 | Karpman | A61B 17/864 | 606/246 |
| 6,217,581 B1 * | 4/2001 | Tolson | A61B 17/8811 | 606/86 R |
| 6,402,758 B1 * | 6/2002 | Tolson | A61B 17/8811 | 606/94 |
| 6,565,572 B2 * | 5/2003 | Chappius | A61B 17/3472 | 600/300 |
| 6,755,835 B2 * | 6/2004 | Schultheiss | A61B 17/8685 | 606/304 |
| 6,887,246 B2 * | 5/2005 | Bhatnagar | A61B 17/8816 | 606/86 R |
| 7,250,055 B1 * | 7/2007 | Vanderwalle | A61B 17/7098 | 606/71 |
| 7,338,493 B1 * | 3/2008 | Vandewalle | A61B 17/686 | 606/86 A |
| 7,354,442 B2 * | 4/2008 | Sasso | A61B 17/8615 | 606/280 |
| 7,608,077 B2 * | 10/2009 | Cragg | A61B 17/1671 | 606/86 R |
| 7,914,537 B2 * | 3/2011 | Boyd | A61B 17/8805 | 606/92 |
| 7,927,339 B2 * | 4/2011 | Ralph | A61B 17/1686 | 606/92 |
| 8,062,270 B2 * | 11/2011 | Sweeney | A61B 17/3472 | 604/264 |
| 8,066,712 B2 * | 11/2011 | Truckai | A61B 17/8811 | 606/92 |
| 8,535,357 B2 * | 9/2013 | Stone | A61B 17/866 | 411/403 |
| 9,050,136 B2 * | 6/2015 | Webb | A61B 17/60 | |
| 2003/0083662 A1 * | 5/2003 | Middleton | A61B 17/0401 | 606/323 |
| 2003/0204189 A1 * | 10/2003 | Cragg | A61B 17/1642 | 606/86 A |
| 2005/0015059 A1 * | 1/2005 | Sweeney | A61B 17/8685 | 604/264 |
| 2005/0055030 A1 * | 3/2005 | Falahee | A61B 17/7098 | 606/92 |
| 2006/0058800 A1 * | 3/2006 | Ainsworth | A61B 17/70 | 606/86 A |
| 2007/0066977 A1 * | 3/2007 | Assell | A61B 17/1757 | 606/96 |
| 2011/0040329 A1 * | 2/2011 | Ainsworth | A61B 17/70 | 606/246 |
| 2011/0245881 A1 * | 10/2011 | Mitchell | A61B 17/7098 | 606/304 |

* cited by examiner

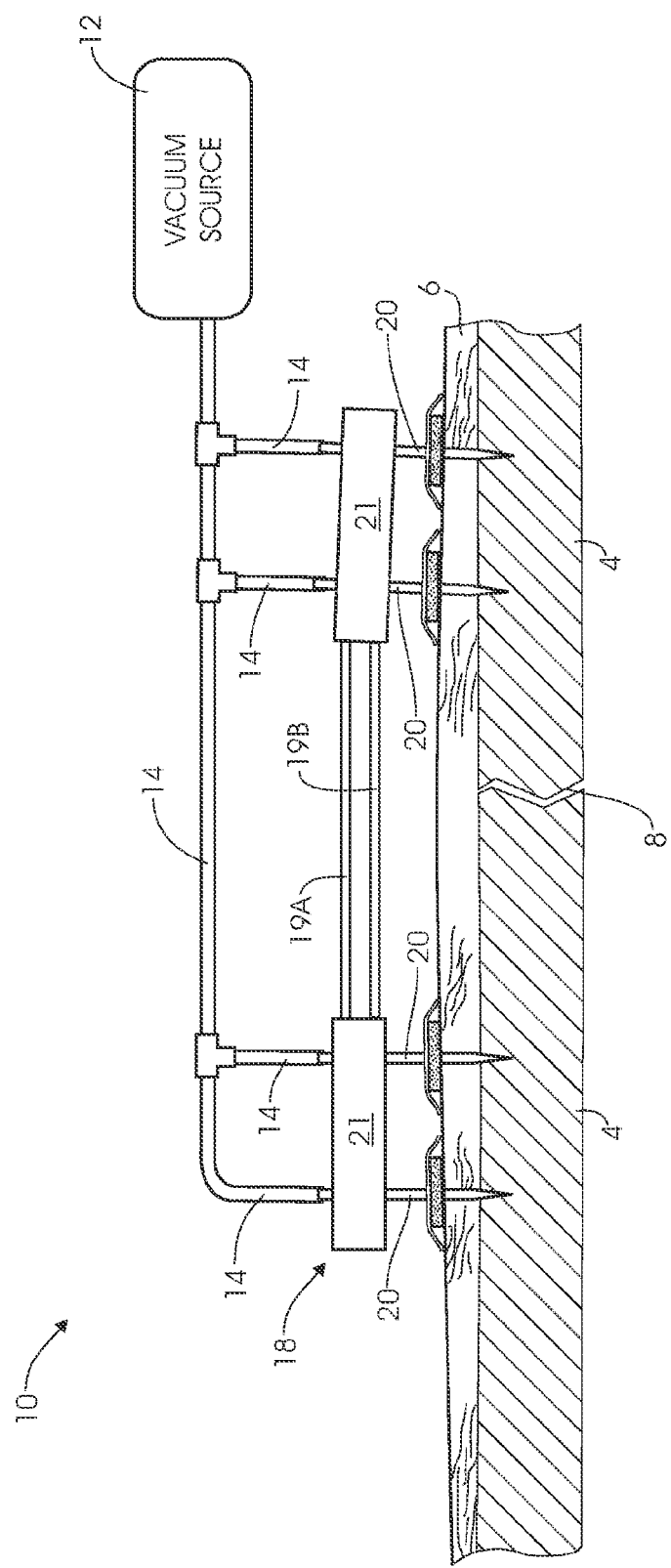

EXTERNAL FIXATION ASSEMBLY AND METHOD OF USE

RELATED APPLICATIONS

This application is a Continuation of U.S. patent application No. 13/896,750, filed May 17, 2013, which is a continuation of U.S. patent application No. 13/094,233, filed Apr. 26, 2011, now U.S. Pat. No. 8,454,603, which is a Divisional of U.S. patent application No. 11/694,395, filed Mar. 30, 2007, now U.S. Pat. No. 7,931,651, which claims the benefit of priority of U.S. Provisional Application No. 60/866,327, filed on Nov. 17, 2006, the entire contents of which applications are incorporated herein by reference.

FIELD OF THE INVENTION

The present invention relates to external fixation, and particularly to fixator pins and devices used in treating bone fractures and deformities with the use of sub-atmospheric pressure.

BACKGROUND

External fixation is a common technique used to treat a variety of conditions, including bone fractures, dislocations, and deformities. Although different techniques are used, external fixation generally involves the use of threaded fixator pins that are screwed into bone. For bone fractures, two or more fixator pins are inserted into the bone on each side of the fracture. Compression and distraction forces are applied to the fixator pins to correctly position and align the bone. External fixation may be applied over several months for complicated fractures, during which time the pin remains in the bone. Long term use of external fixator pins involves risks and complications that can delay the patient's recovery and further aggravate the patient's condition. In some patients, the pin may result in infection within the pin tract in the bone. In addition, the skin around the pin/skin interface can become irritated or infected. The pin may also become unstable and loosened in the bone. Therefore, there is a need for improved implements and devices that reduce the risks and complications associated with external fixation.

SUMMARY OF THE INVENTION

Based on the foregoing, an external fixation assembly includes a plurality of hollow fixator pins for insertion into a patient's bone. Each pin has a hollow shaft with an insertion end that may be advanced through a tissue opening and into the patient's bone. The shaft has an interior passageway or conduit such as a bore that extends generally along the longitudinal axis of the shaft. At least one vent aperture, and optionally a plurality of vent apertures, extend through the shaft in fluid communication with the bore. The pin may be removably connected to a source of vacuum pressure operable to draw fluid or gas through the aperture of the pin and apply reduced pressure in the tissue surrounding the pin. The reduced pressure may be used to stimulate blood circulation around the tissue opening, reduce the potential for inflammation and infection, and stabilize the fixator pin in the bone.

The shaft may include a first inner section or insertion end, such as a threaded section, for securing the fixator pin in the bone. In addition, the shaft may include a second outer section, such as a non-threaded section. A connection port is provided on the shaft, for example, along or at an end of the outer section to fluidly connect to or communicate with the bore inside the pin. The port may be connected to the source of vacuum pressure by a suitable connection such as a flexible tube. A cover is removably disposed around the pin and surrounds the tissue opening to form a generally fluid-tight enclosure that is sufficient to enable sub-atmospheric pressure, i.e., negative pressure, to be maintained beneath the cover. A pressure distribution element, such as a porous screen, may additionally be placed at or around the pin and between the tissue opening and the cover to prevent sub-atmospheric pressure to be distributed beneath the cover and at the tissue opening and, optionally, to substantially prevent direct contact between the tissue opening and the cover.

If a plurality of vent apertures are utilized, the apertures may be located on one or more sections of the shaft to apply reduced pressure to different selected locations along the shaft and optionally to different tissue areas. For example, the apertures may be formed in the outer or non-threaded section of the shaft and adapted to apply reduced pressure at the epidermis or external to the epidermis. In addition, the apertures may be formed in the inner or threaded section and adapted to apply a reduced pressure in the pin tract in the bone. Alternatively, the apertures may be formed in two separate areas on the non-threaded section of the shaft to apply reduced pressure for example, to one or more of a sub-cutaneous layer or organ, the epidermis and/or a tissue layer in the dermis. As yet a further alternative, apertures may be provided in the inner or threaded section as well as the outer or non-threaded section, as well as along different areas of the outer section, to supply reduced pressure at any one or all of the bone, sub-cutaneous tissue or organs, the dermis, the epidermis, and to areas beneath the cover and outside of the epidermis, or any other selected tissues or organs enclosed and sealed within the cover.

A method for applying external fixation using the hollow fixator pins described above includes the step of inserting each pin through a skin opening and into bone. The pin is positioned so that the apertures are in substantial alignment with selected tissue. For example, the apertures could be aligned with the epidermis, or positioned inside the pin tract in the bone or at other desired locations. Once the pins are placed, the skin opening around each pin is covered with a sealed enclosure. The hollow pins are connected to a source of vacuum pressure. The source of vacuum pressure functions to create reduced pressure that is supplied from the pin apertures in the patient's bone tissue or any soft tissues outside of the bone as desired.

DESCRIPTION OF THE DRAWINGS

The foregoing summary as well as the following description will be better understood when read in conjunction with the Figures in which:

FIG. 1 is a schematic view of an external fixation assembly in accordance with the present invention.

DETAILED DESCRIPTION OF THE PREFERRED EMBODIMENT

Figure 2A:
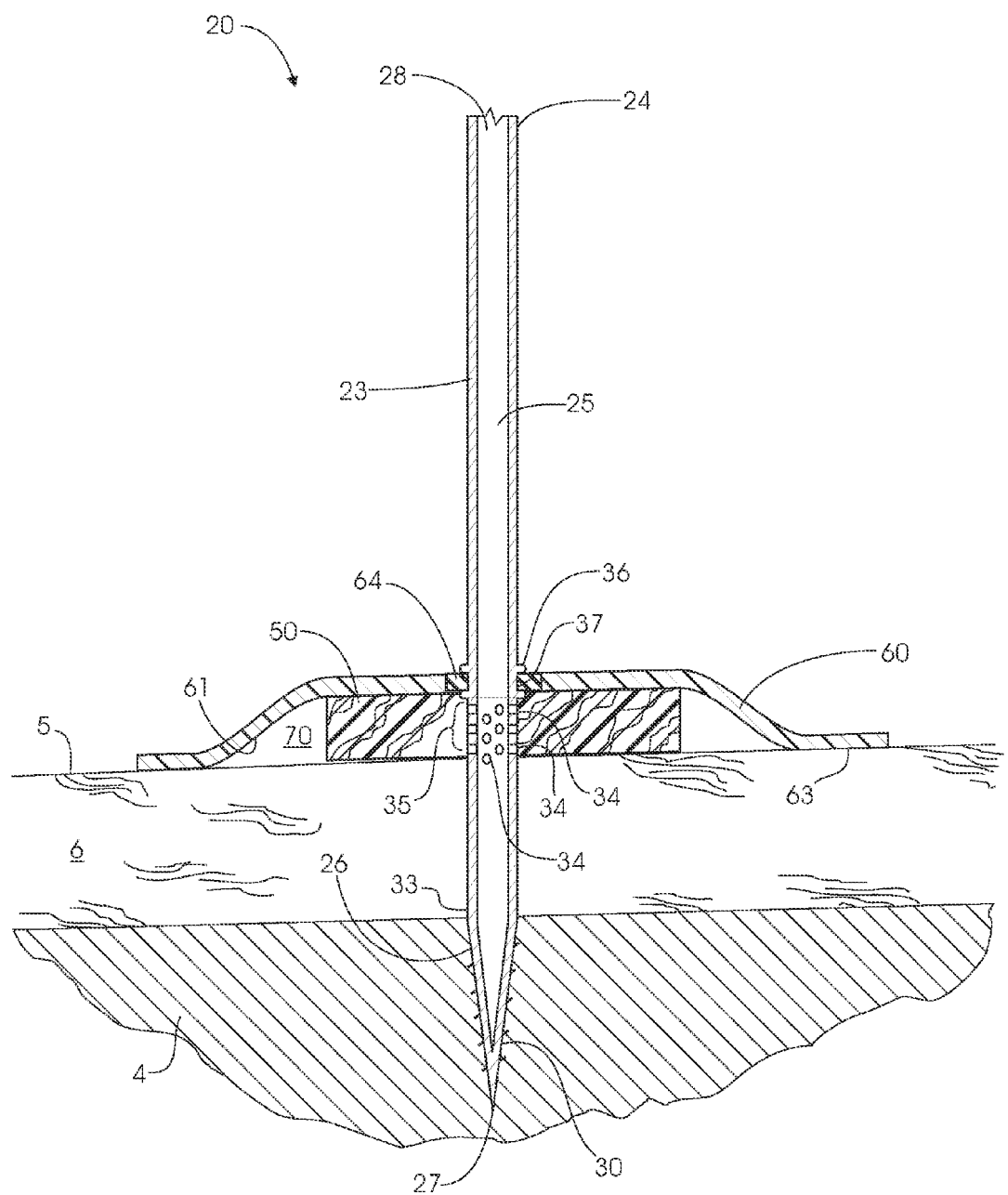
FIG. 2A is a cross-sectional view of components used in accordance with the present invention, featuring a first embodiment of a fixator pin.

Referring now to the drawing figures in general, and to FIG. 1 specifically, an external fixator assembly 10 is shown in accordance with the invention. In general, the fixator assembly may include four hollow fixator pins 20 inserted into bone tissue 4 in the patient on opposite sides of a fracture or other deformity 8 so that suitable compression or distraction forces can be applied. Each fixator pin 20 is positioned at a pin site and connected to a source of vacuum pressure 12. Negative or reduced pressure, e.g., sub-atmospheric pressure, is applied at each pin site to stimulate blood circulation to the pin site, to reduce the potential for inflammation and infection, and to stabilize the fixator pin. While each of the fixator pins 20 shown in FIG. 1 is a cannulated pin for supplying reduced pressure, other fixator arrangements could be utilized in which one or more fixation pins are cannulated while one or more other pins are not cannulated. The non-cannulated pins may be used at pin sites where the application of reduced pressure is contraindicated or is not desired or needed.

Each cannulated fixator pin 20 has a hollow shaft and sidewall 23 that forms an internal bore 25. The fixator pin 20 may be cannulated from an outer end 24 to provide an access port 28 at the outer port end that leads to the internal bore that extends from the outer end 24 to the inner or tip end 27 of the pin. To preserve the integrity of the tip, the bore 25 may terminate before extending through the tip end. The fixator pin 20 is removably connected to the source of vacuum pressure 12 by suitable connectors or tubing 14, such as flexible tubes, removably coupled to the port end 24 of the pin 20. One or more vent apertures 34 extend through the sidewall 23 of the fixator pin 20 and communicate with the bore in the shaft. The source of vacuum pressure 12 is operable to draw fluid or gas through the apertures 34 and bore 25 to create negative pressure at the interface between the pin and tissue around the pin.

Referring now to FIGS. 1-2, the external fixator assembly 10 will be described in more detail. For purposes of clarity, the fixator assembly 10 is shown in simplified form with a fixator device 18 having two fixator pins 20 on each side of a bone fracture or other deformity 8. It will be appreciated that more than two fixator pins 20 may be inserted on each side of the bone fracture 8, depending on the location and nature of the fracture. In addition, it will be appreciated that the fixator assembly 10 is not strictly intended for bone fractures, and may be applied to other conditions, including for example, dislocations and deformities. The assembly 10 may incorporate a variety of fixator devices, and the specific type of fixator is not critical. For example, the fixator assembly 10 may be used with flexible or rigid fixators. In addition, the fixator assembly 10 may be applied to different fracture types and fracture locations, including for example, femural fractures and tibial fractures.

The fixator 18 includes a pair of retainers 21, with each retainer positioned on one side of the bone fracture 8. One or more bars connect between the retainers 21 and are operable to apply compression and distraction forces on the fixator pins. In FIG. 1, the retainers 21 are connected, for example, by a compression bar 19A and a distraction bar 19B.

Referring now to FIG. 2A, a fixator pin 20 is shown having a hollow or cannulated shaft 23 with an attachment end 24 (the port end) and an insertion end 26 (the tip end). The bore 25 extends through the hollow shaft 23 of the cannulated fixator pin 20 and provides fluid communication from the attachment end 24 to the insertion end 26. A vacuum port 28 is formed at or through the attachment end 24 of the shaft 23 and is in fluid communication with the bore 25. The attachment end 24 is adapted to receive an end of flexible tubing 14 in a sealed, snug fit as the tube slides over the attachment end 24 to provide a fluid flow path to the vacuum port 28, as shown in FIG. 1. The flexible tubing 14 has an interior lumen with a diameter substantially equal to the outer diameter of the fixator pin 20. As such, the flexible tubing 14 is configured to slide over the attachment end 24 of the fixator pin 20 and form a substantially fluid-tight seal. The flexible tube 14 connects the fixator pin 20 with a source of vacuum pressure 12. A variety of vacuum pressure sources may be used with the fixator assembly 10, including, for example a Gast Vacuum pump (Fischer Scientific).

Figure 7A:
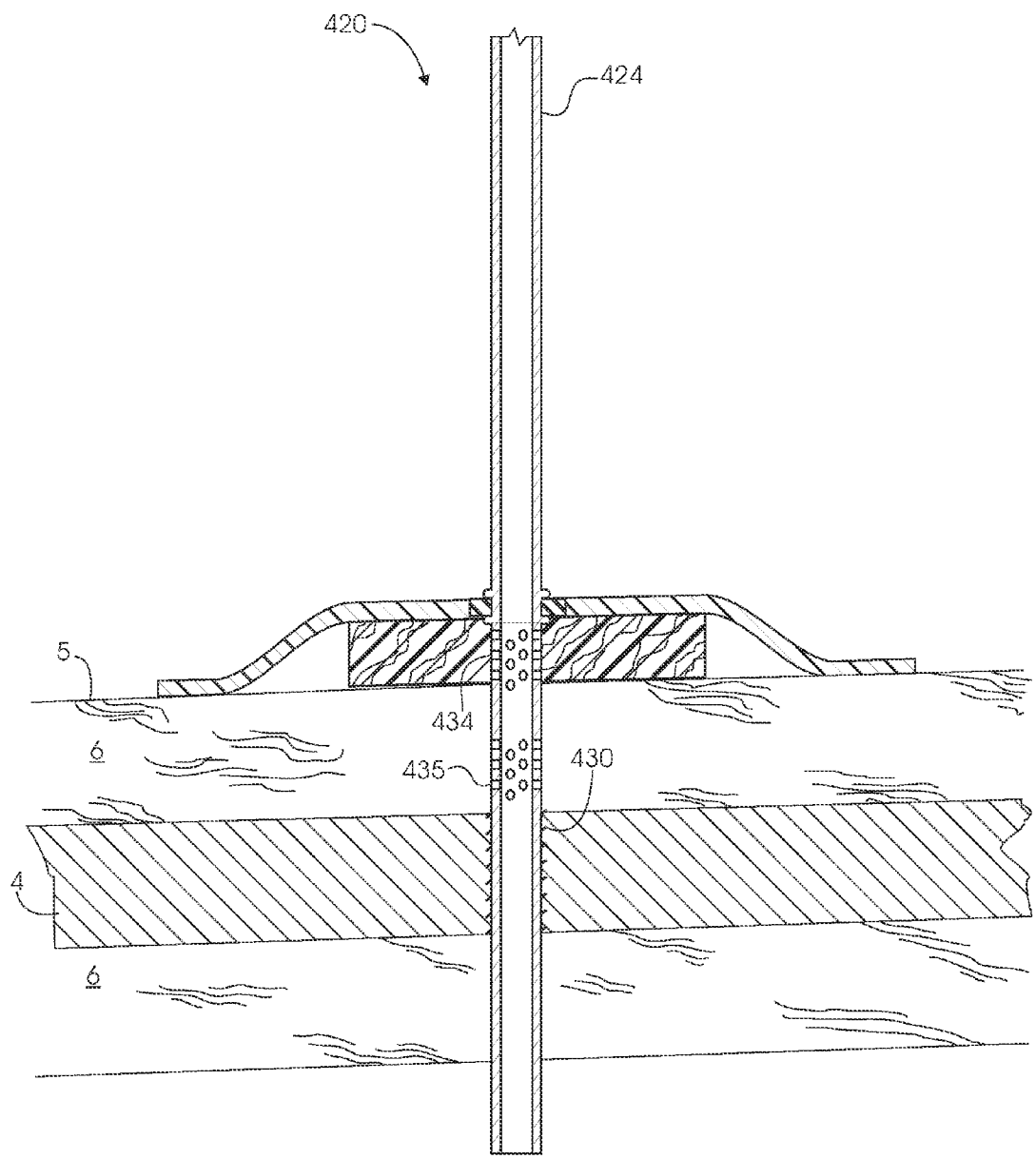
FIGS. 7A and 7B are cross-sectional view of components used in accordance with the present invention, featuring a fourth embodiment of a fixator pin.
Figure 7B:
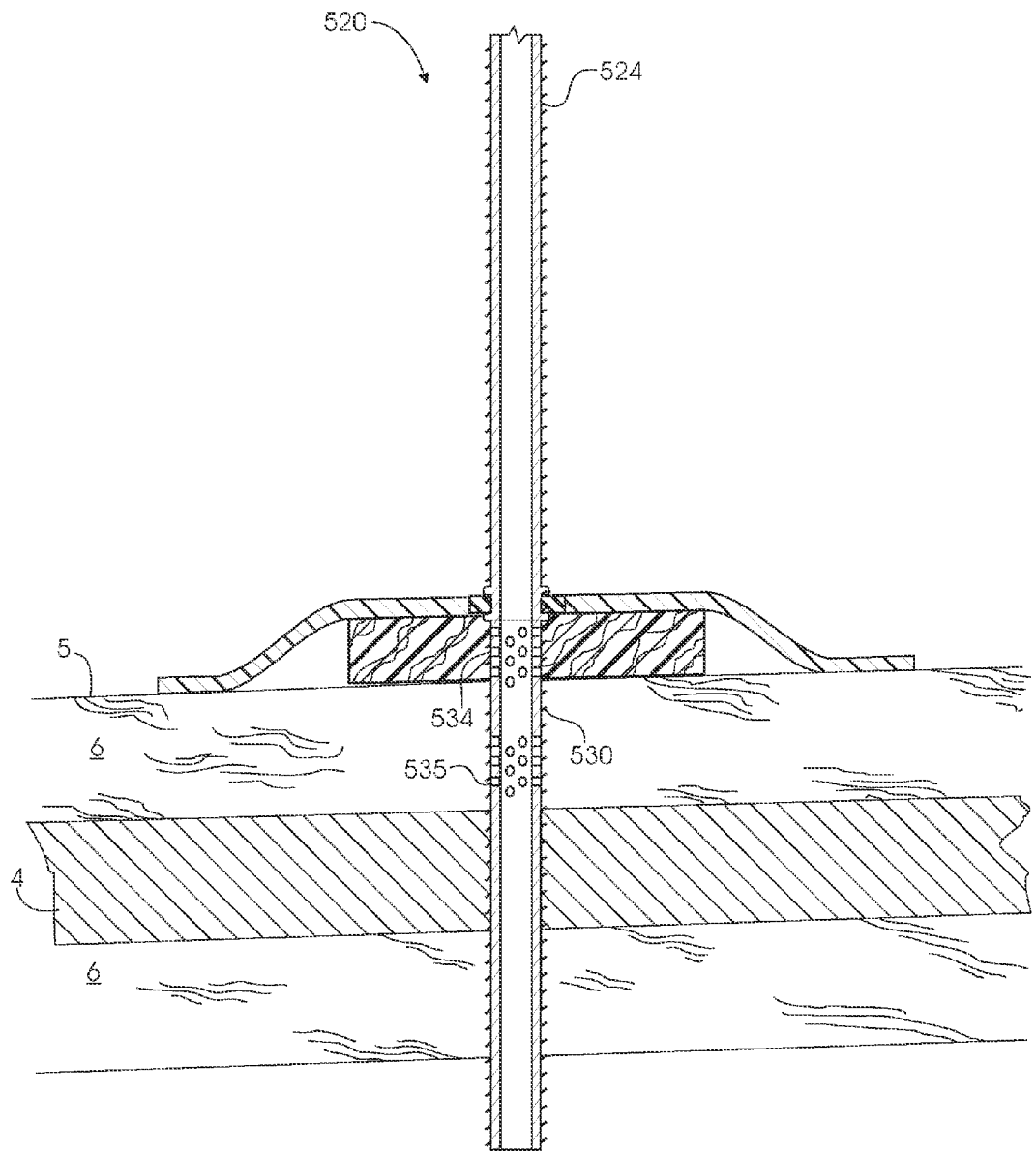

The pin 20 has a first threaded section 30 that may taper to form a sharp point or tip 27, and a second non-threaded section 33. The pin 20 may have other configurations wherein the tip end does not taper to a point or does not taper at all. The threaded section 30 is configured to penetrate into the bone 4 to securely anchor the fixator pin 20 into the pin tract in the bone 4. For this purpose, the pin may include a self-tapping threaded tip 27 for tapping into bone 4. Alternatively, the fixator pin may be provided in the from of a transfixing pin 420, 520 for positioning through a limb, FIGS. 7A and 7B. In such a use, the pin 420 may have a threaded middle portion 430 with smooth end portions or the entire pin 520 may be threaded 530, and the pin 420, 520 may be provided with a Trocar tip. Vent apertures 435, 535 may be provided in the middle portion of the pin 420, 520 or may be provided peripherally, e.g., vent apertures 434, 534.

Figure 2B:
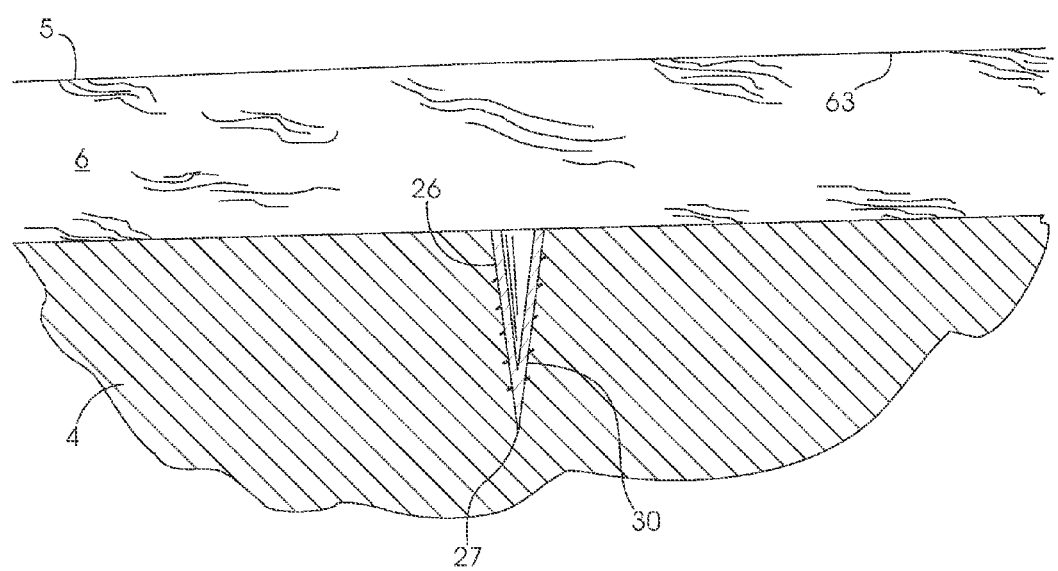
FIG. 2B is a cross-sectional view of components used in accordance with the present invention, featuring an implantable pin portion.

As shown schematically in FIG. 2A, the pin 20 screws into the bone 4 to hold the pin firmly in place. For this purpose, the pin 20 may be screwed into the bone a desired depth greater than that specifically depicted in FIG. 2A so that the non-tapered portion 33 extends into the bone to anchor the pin in place. Optionally, a portion of the pin 20, such as tip 27, may be detachable to provide an implant that may be left in the patient, as shown in FIG. 2B. In such a configuration the pin 20, or the implant portion, e.g. tip 27, may comprise a bone substitute material. For example, the pin 20 or tip 27 may comprise a natural, synthetic, or natural-synthetic hybrid porous material, and may comprise a material to support or direct osteoconduction or a material to induce differentiation of stem cells to osteogenic cells, i.e. osteoinductive agents, or materials which provide stem cells, e.g. bone marrow aspirate.

For example, the pin 20 or tip 27 may be a bioglass, ceramic material, or other natural or synthetic porous material, such as calcium sulphate or calcium phosphate. One suitable calcium sulphate bone substitute is OSTEOSET® Bone Graft Substitute, a product of Wright Medical Technology, Inc. of Arlington, Tenn. Another class of suitable materials is one comprising various derivates of calcium phosphate, which can be used to provide a structural matrix for osteoconduction, such as hydroxyapatite (coral based or chemically derived synthetic ceramic), fluorapatite, tri-calcium phosphate, bioglass ceramics and combinations thereof. One suitable calcium phosphate bone substitute is OsteoGraft™ Bone Graft Substitute, a product of Millenium Biologix of Kingston, Ontario, Canada. In addition, the pin 20 or tip 27 need not comprise a bone substitute material and may comprise a metal or other suitable materials.

Figure 8:
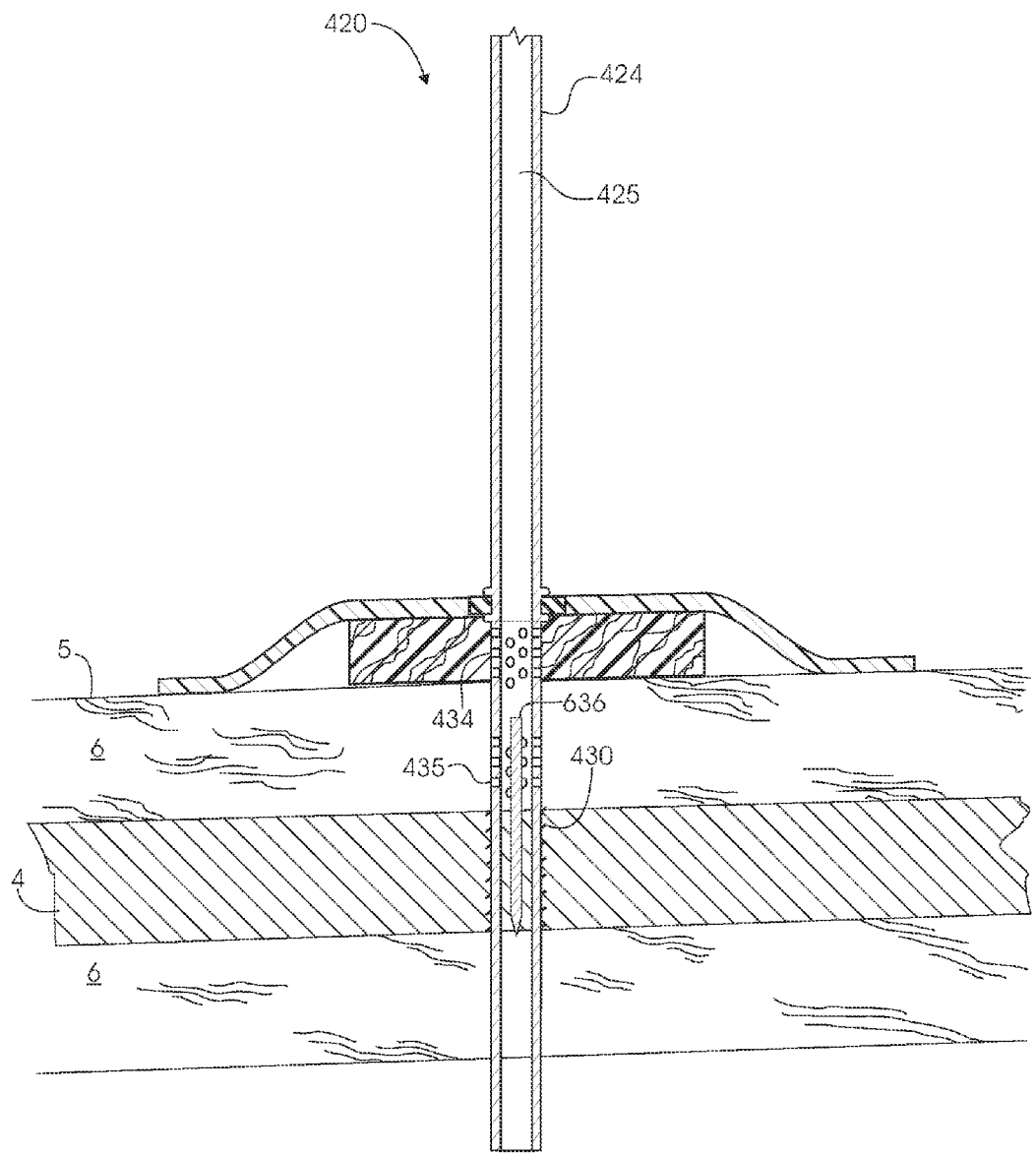
FIG. 8 is a cross-sectional view of components used in accordance with the present invention, featuring a guide pin used in conjunction with a fixator pin.

In addition, a guide pin 636 may be used in conjunction with the open-ended fixator pin 424 to aid in guiding placement of the fixator pin 424, FIG. 8. For instance, a narrow guide pin 636 having a cross-sectional dimension less than that of the bore 425 may be placed in the bone 4 prior to placement of the fixator pin 424, allowing the physician to first verify that the guide pin 636 has been placed in the correct location. The location of the guide pin 636 may be determined by an x-ray or other suitable imaging modality. After the guide pin location has been verified, the fixator pin 424 may be inserted in the bone 4 by placing the fixator pin 424 over the guide pin 636 so that the guide pin 636 is located within the bore 425 of the fixator pin.

Figure 3:
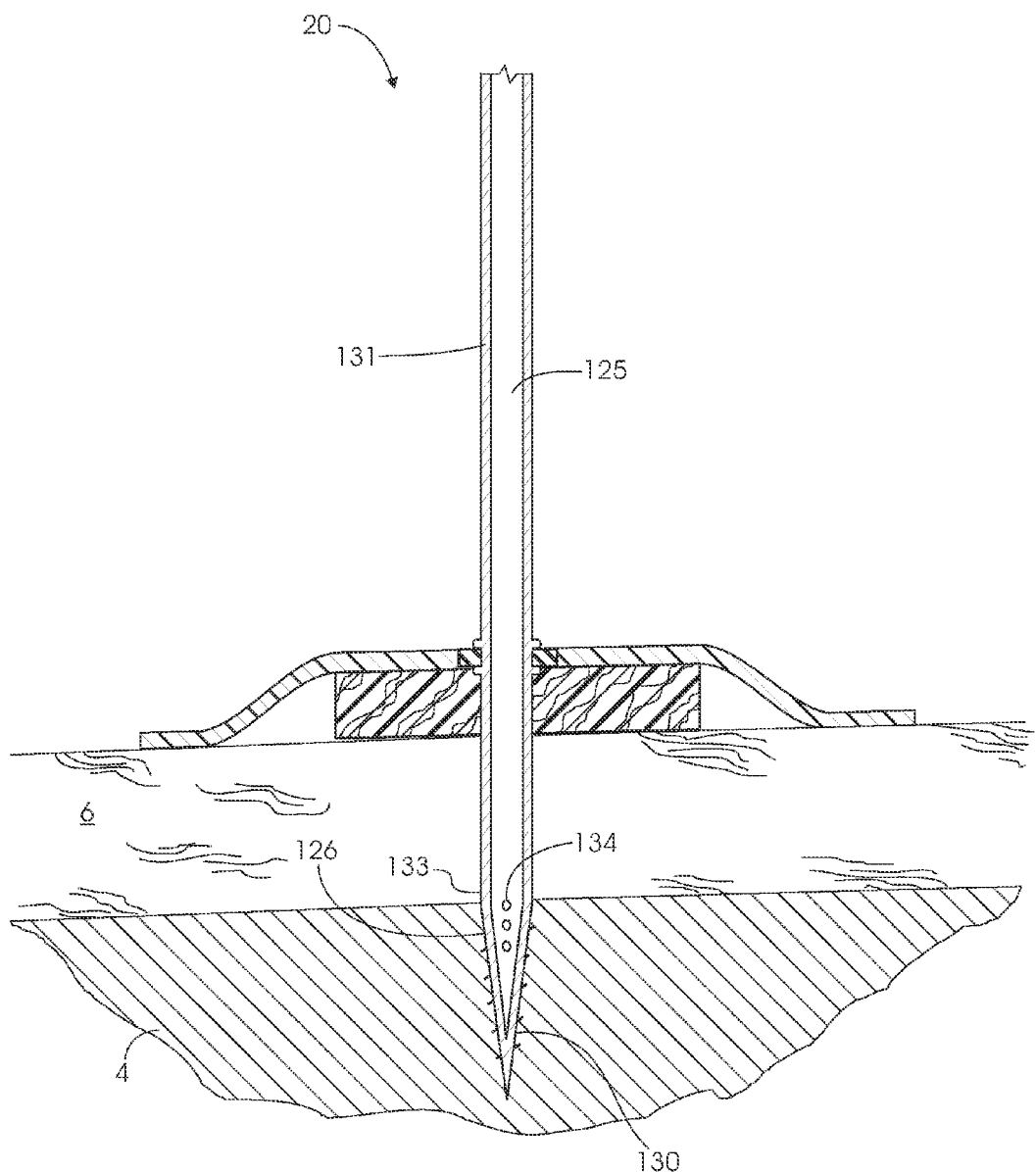
FIG. 3 is a cross-sectional view of components used in accordance with the present invention, featuring a second embodiment of a fixator pin.
Figure 6:
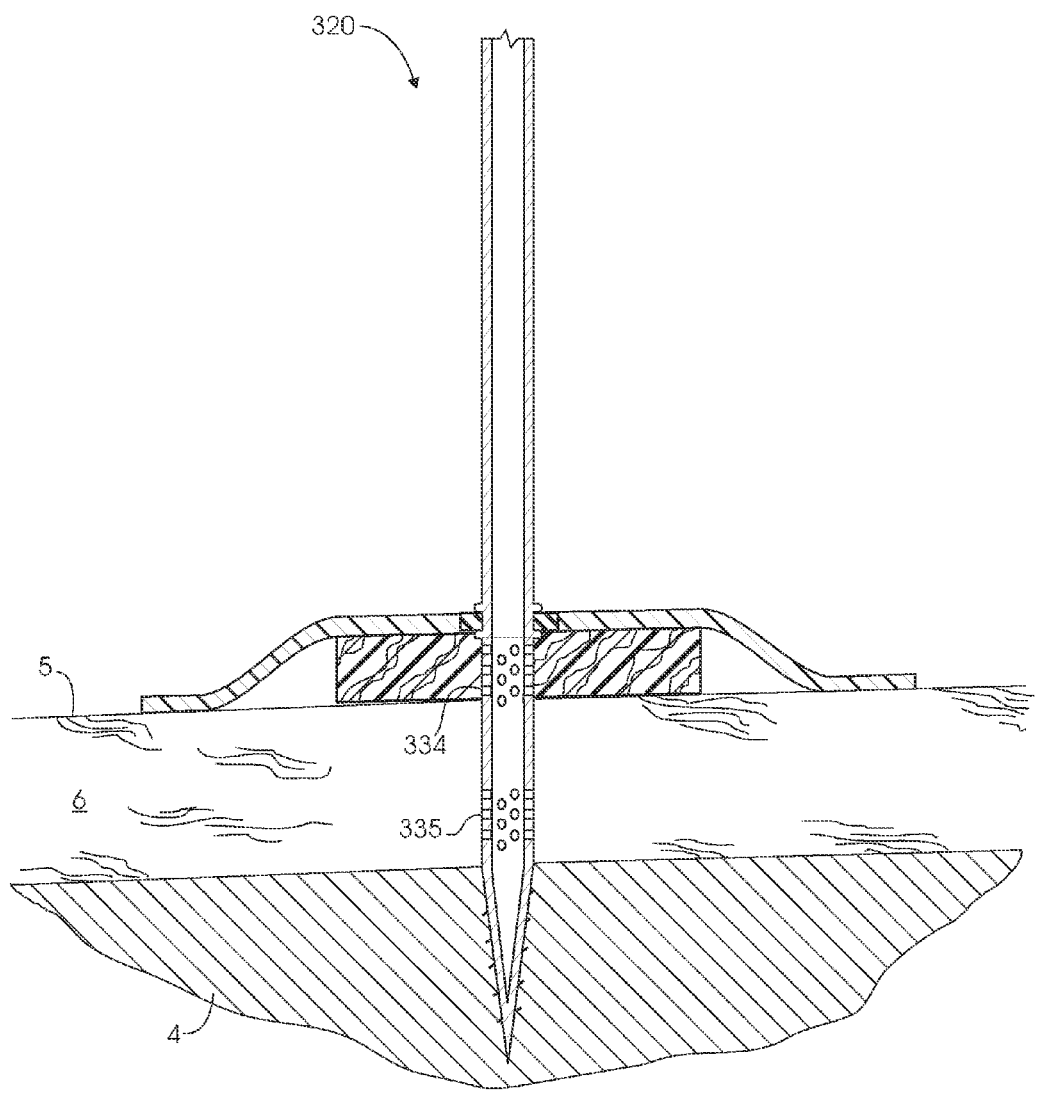
FIG. 6 is a cross-sectional view of components used in accordance with the present invention, featuring a fourth embodiment of a fixator pin.

Returning now to FIG. 2A, a plurality of apertures 34 may formed through the non-threaded section 33 of the shaft 23 to form a vent section 35 along the length of the shaft. The apertures 34 extend through the wall of the shaft 23. When the vacuum pump 12 is activated, the vacuum pump draws air or gas through the apertures 34 to create negative pressure through and along the apertures. The apertures 34 may be positioned at various locations relative to the tip 27 to apply reduced pressure at specific areas within the pin tract. For example, the apertures 34 may be positioned where the pin intersects with the epidermis 5 ("skin/pin interface"), as shown in FIG. 2. In this arrangement, the apertures may form a vent section 35 at a location at and above the epidermis to supply negative pressure through a reduced-pressure distribution element or screen 50. Alternatively, the apertures 34 may be positioned where the pin intersects deeper tissue layers in the dermis 6. Apertures may be concentrated at one section of the shaft 23 to treat a specific tissue layer, or may be formed at multiple sections of the shaft to supply reduced pressure to multiple layers or tissues. In FIG. 6, a second embodiment of a fixator pin 320 is shown with apertures 334 positioned at one section of the shaft to supply reduced pressure at the skin/pin interface and apertures 335 positioned at another section of the shaft to supply reduced pressure at deeper tissue layers in the dermis 6. As shown in FIG. 3, the tip end of the fixator pin 120 may also include apertures 134 to supply reduced pressure to bone 4 at the pin/bone interface. The pins 20, 120, 220, 320, 420, 520 may also be used intermittently or continuously to effect delivery of medication, such as antibiotics, local anesthetic, and biopharmaceuticals, to the various tissue/pin interfaces by introducing medication into the bore for delivery through the vent apertures.

A fluid-tight enclosure or cover 60, such as OpSite or TEGADERM, is positioned over the pin 20 to cover the pin site. The cover 60 is configured to form a fluid-tight seal around the pin site to maintain the reduced pressure that is applied at the tissue/pin interface. The cover 60 includes an inner face that faces into the pin site, and an outer face that faces outwardly and away from the pin site when the cover is placed over the pin 20. The inner face may include an adhesive backing 61 that adheres to the patient's skin around the periphery 63 of the pin site. Alternatively, or in addition, other adhesives or sealers may be applied. The adhesive backing has sufficient adhesive properties to form a fluid-tight enclosure around the periphery of the pin site and to hold the cover 60 in sealed contact with the patient's skin when reduced pressure is applied beneath the cover. The cover may be impermeable or semipermeable depending on the level of permeability needed or desired for a particular application as long as the desired level of reduced pressure is maintained beneath the cover for a desired amount of time to effect the desired treatment.

A hole or opening 37 is formed through a central or interior portion of the cover 60 and is adapted to fit over the attachment end 24 of the fixator pin 20 as the attachment end 24 of the pin is inserted through the hole 37. The cover 60 engages the outer circumference of the pin in a fluid tight seal to substantially prevent leakage of pressure through the hole around the pin. Optionally, the cover 60 may incorporate an O-ring seal 64 at the hole 37 in the cover that is adapted to squeeze around and seal onto the outer periphery of the pin. The O-ring 64 engages the exterior of the fixator pin 20 when the cover is placed over the pin. The O-ring 64 has an inner diameter substantially equal to the outer diameter of the fixator pin 20 and is configured to frictionally engage the outer surface of the pin. The O-ring 64 may be affixed to the cover 60 around the hole 37 by an adhesive or other bonding. Alternatively, the O-ring may be embedded within the cover or heat sealed into the cover. For example, the cover 60 may include two plies that form a pocket in which the O-ring 64 is embedded. The frictional engagement between the O-ring 64 and pin 20 forms a fluid-tight seal between the exterior of the pin and the cover.

It may be desirable to stabilize the O-ring axially on the pin 20. Referring to FIG. 2A, the pin 20 includes a pair of circumferential ridges 36 on the outer section of the pin that form a seat for the O-ring 64. The ridges 36 form a narrow groove having a thickness and diameter suitable to seat the O-ring 64. The groove is adapted to receive the O-ring when the cover is placed over the pin 20. As a result, the seat formed by the ridges 36 limits the axial displacement of the O-ring 64 and cover 60 along the length of the pin 20. The O-ring may be formed of any flexible elastomeric material that permits the O-ring to be stretched. In this way, the O-ring 64 can be stretched to temporarily expand the inside diameter of the O-ring to allow it to be slipped over the top ridge and into the seat allowing the O-ring to slide into and become properly seated within the seat groove.

A reduced-pressure distribution element such as a porous screen 50 may surround the apertures 34 on the fixator pin 20 as shown in FIG. 2A. The screen 50 is positioned beneath the cover 60 and over the pin site to help distribute reduced pressure across its surface area and to optionally help keep the cover out of direct contact with the skin around the pin 20. The screen 50 has sufficient porosity to permit the flow of gases into the apertures of the pin when reduced pressure is applied by the vacuum pump. The screen 50 may also absorb exudate and other liquids that may aspirate from the tissue around the pin site. Preferably, the screen 50 is formed out of an open cell polymer foam, such as polyurethane foam. Other porous or perforated materials may also be used. Foams may be used with a wide range of pore sizes and densities. Since the fixator assembly 10 usually rests on top of the patient's extremity, it may be desirable to select a light-weight low density foam or sponge that is less noticeable to the patient. It may optionally be desirable to form large perforations or other flow paths in the screen 50 to reduce the weight of the screen or to increase the flow of gas drawn by the vacuum pump. In FIG. 2A, the screen 50 and cover 60 are cut to fit over a single pin site. Other screen and cover configurations may be used, however, and the configurations illustrated in the drawing figures are not intended to be the only workable configurations. For example, it may be desirable to use a single screen 50 and cover 60 over multiple pin sites. This may be desirable where pins are spaced close together in a relatively small area.

The fixator assembly 10 may be used in the following manner. After the pin locations are selected, small incisions are made through the skin at the pin locations, and the fixator pins 20 are placed into the patient's bone. The desired pin location may include a fracture or a joint to be immobilized. In such a case where the pin 20 is inserted in the fracture or joint, the pin 20 may desirably include an implantable portion which may optionally comprises a bone substitute material. The pins 20 are advanced into the bone until the pin apertures are positioned at a desired axial locations relative to the tissue/pin interface. For example, as shown in FIG. 2A, the apertures 34 may be positioned at the skin/pin interface in substantial alignment at, with or above the epidermis 5 or in communication with the screen 50. Alternatively, as shown in FIG. 6, the apertures 335 may also be positioned adjacent to tissue in the dermis 6 either exclusively or in conjunction with apertures at another location such apertures 334 at or above the epidermis 5. Apertures may be provided at other locations as well. Screens 50 are secured over the pins around the apertures and over the incisions. Covers 60 are then placed over the pins 20, and the adhesive surfaces on the inner faces of the covers are pressed firmly against the patient's skin to form a fluid tight enclosure around the pin sites. Many types of suitable covers may be used. The fixator 18 is then assembled and connected with the fixator pins. Once the fixator 18 is assembled, flexible tubes 14 are connected to the attachment ends of the fixator pins 20 and to the suction port of the vacuum pump 12.

The vacuum pump 12 is connected to a power source and switched on to apply reduced pressure within the space 70 beneath the cover 60 as shown in FIG. 2A. The amount of pressure reduction applied at the pin sites is dependent on the desired course of treatment, the location of the pins, the density of the screen material, and other variables. For example, the reduced pressure may be between 10 mm Hg below atmospheric pressure and 300 mm Hg below atmospheric pressure. In the embodiment shown in FIG. 3, reduced pressure is supplied to the pin/bone interface at apertures 134 while the cover and optional screen help to maintain the negative pressure at that site.

Thus far, the fixator pins have been described primarily with apertures that are positioned to apply reduced pressure at the epidermis and/or dermis. It will be appreciated that reduced pressure may be applied at deeper levels in the pin incision and need not be limited to the dermis or epidermis. For example, reduced pressure may be applied, as shown in FIG. 3, at the interface between the fixator pin and bone ("bone/pin interface") by apertures 134 positioned at the bone 4 of FIG. 3. Application of reduced pressure in bone tissue is intended to reduce the occurrence of pin tract infection and inflammation in the bone. In addition, the application of reduced pressure in bone tissue is intended to increase bone growth and bone ingrowth in the pin tract, which increases stability of the pin.

Figure 4:
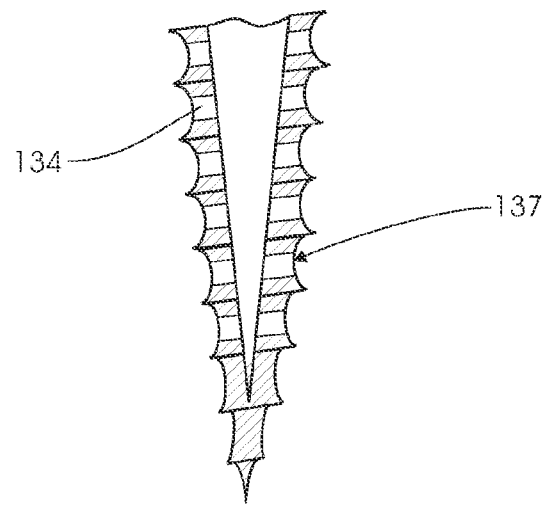
FIG. 4 is an enlarged cross-sectional view of a threaded section of the fixator pin of FIG. 3, broken away at one end for clarity.

Referring now more specifically to FIG. 3, a third embodiment of a fixator pin 120 is shown. The fixator pin 120 is configured to apply reduced pressure at the bone/pin interface in a pin tract. The fixator pin 120 is substantially similar to the pins described above, having a hollow shaft 131 with a central bore 125, an insertion end 126, a threaded section 130 on the insertion end, a non-threaded section 133, and a plurality of apertures 134. The apertures 134 are formed in the threaded section 130 of the insertion end 126 as opposed to the non-threaded section 133 of the shaft. In this way, the reduced pressure is applied through bore 125 to the pin tract inside the bone 4. Referring to FIG. 4, the apertures 134 are preferably recessed in the groove formed by the thread on the threaded section at the tip 137. The groove provides additional void space around the apertures to reduce the potential for clogging caused by bone fragments that may become lodged in the apertures.

Figure 5:
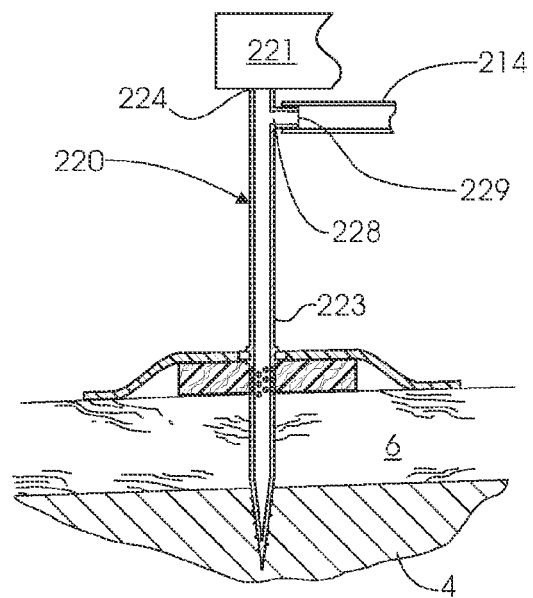
FIG. 5 is a cross-sectional view of components used in accordance with the present invention, featuring a third embodiment of a fixator pin.

In some cases, it may be desirable to locate the vacuum port as a side port on the side of the pin, rather than at the attachment end. For example, the fixator appliance may have retainers that connect over the top of the fixator pins, covering the attachment ends of the pins and preventing connection of flexible tubing to the attachment ends. Therefore, locating the vacuum port on the side of the pin can avoid problems that occur when the attachment end is obstructed or inaccessible. In FIG. 5, a fourth embodiment of a fixator pin 220 is shown in accordance with the invention. The fixator pin 220 is connected to a retainer 221 that covers the end of the fixator pin. A vacuum port 228 is formed through the side wall of the pin 220 and connects with a flexible tube 214. A cylindrical hub 229 surrounds the vacuum port 228 and projects radially outwardly from the side wall of the pin 220. The flexible tube 214 is adapted to slide over the hub 229 to connect the port 228 to a vacuum pump or other source of reduced pressure. The hub 229 has an outer diameter that is substantially equal to the inner diameter of the flexible tube 214. In this way, the flexible tube slides over the hub in frictional engagement to form a fluid-tight seal around the port 228.

The terms and expressions which have been employed are used as terms of description and not of limitation. There is no intention in the use of such terms and expressions of excluding any equivalents of the features shown and described or portions thereof. It is recognized, therefore, that various modifications are possible within the scope and spirit of the invention. Accordingly, the invention incorporates variations that fall within the scope of the following claims.

What is claimed is:

1. An external fixation assembly for applying a compression and/or distraction force to a bone to be treated, comprising:
   a plurality of fixator pins, wherein each fixator pin comprises:
   a hollow shaft having an attachment end for connection to a supply of reduced pressure and an insertion end for inserting into bone, the shaft forming a fluid passageway that extends along a longitudinal axis of the shaft;
   a first section on the shaft for securing the pin in the bone;
   a second section on the shaft at the attachment end having a port in communication with the fluid passageway;
   at least one aperture that extends through a wall of the shaft in fluid communication with the passageway to transmit reduced pressure internally and externally of the shaft,
   wherein each fixator pin includes stem cells;
   at least one bar connected between a respective pair of the plurality of pins proximate the attachment ends of the pins to provide a compression and/or distraction force therebetween; and
   a vacuum source operably connected to the port.

2. An external fixation assembly for applying a compression and/or distraction force to a bone to be treated, comprising:
- a plurality of fixator pins wherein each fixator pin comprises:
- a hollow shaft having an attachment end for connection to a supply of reduced pressure and an insertion end for inserting into bone, the shaft forming a fluid passageway that extends along a longitudinal axis of the shaft;
- a first section on the shaft for securing the pin in the bone;
- a second section on the shaft at the attachment end having a port in communication with the fluid passageway;
- at least one aperture that extends through a wall of the shaft in fluid communication with the passageway to transmit reduced pressure internally and externally of the shaft,
- wherein each fixator pin includes a material to induce differentiation of stem cells to osteogenic cells;
- at least one bar connected between a respective pair of the plurality of pins proximate the attachment ends of the pins to provide a compression and/or distraction force therebetween; and
- a vacuum source operably connected to the port.

* * * * *